United States Patent [19]
Rondeau et al.

[11] Patent Number: 5,810,713
[45] Date of Patent: Sep. 22, 1998

[54] AUTOCLAVABLE ENDOSCOPE

[75] Inventors: Michel Y. Rondeau, San Jose, Calif.;
David J. Collette, San Antonio, Tex.;
Christine Decaria, Sunnyvale, Calif.

[73] Assignees: Valquest Medical, Inc.; Fibotech, Inc., both of San Jose, Calif.

[21] Appl. No.: 678,620

[22] Filed: Jul. 10, 1996

[51] Int. Cl.⁶ .................................................... A61B 1/04
[52] U.S. Cl. ............................................ 600/133; 600/160
[58] Field of Search ...................... 600/160, 161, 600/175, 176, 177, 182, 128, 129; 385/115, 116

[56] References Cited

U.S. PATENT DOCUMENTS 4,790,295 12/1988 Tashiro ................................. 600/182 X
5,339,800 8/1994 Wiita et al. .......................... 600/157 X

*Primary Examiner*—Beverly M. Flanagan
*Attorney, Agent, or Firm*—Robert O. Guillot

[57] ABSTRACT

The flexible endoscopic probe of the present invention includes mechanically engaged components within the tip of the probe. That is, the probe includes a viewing system including a coherent optical fiber having a lens that is mechanically engaged to the tip thereof. Additionally, a metal sleeve may be utilized at the tip of the probe to mechanically bind all of the components within the probe at its tip. Potting materials or adhesives may also be utilized to seal the components within the probe tip. Owing to the usage of mechanical binding methods, the probe is more durable and may be heat sterilized in an autoclave, or the like, in order to permit repeated usage of the probe.

10 Claims, 3 Drawing Sheets

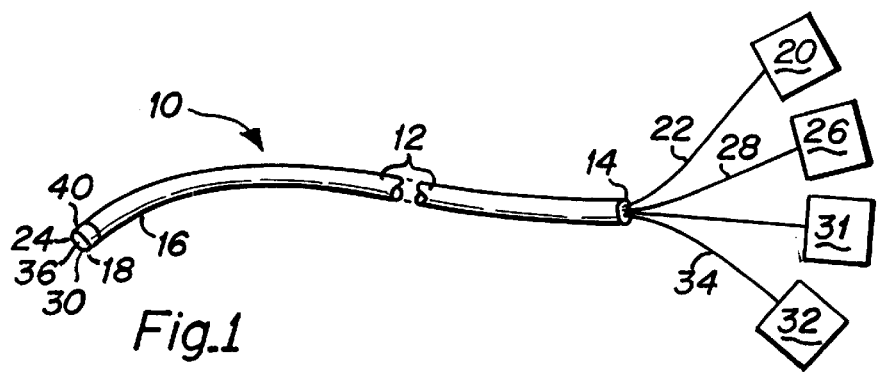
Fig. 1
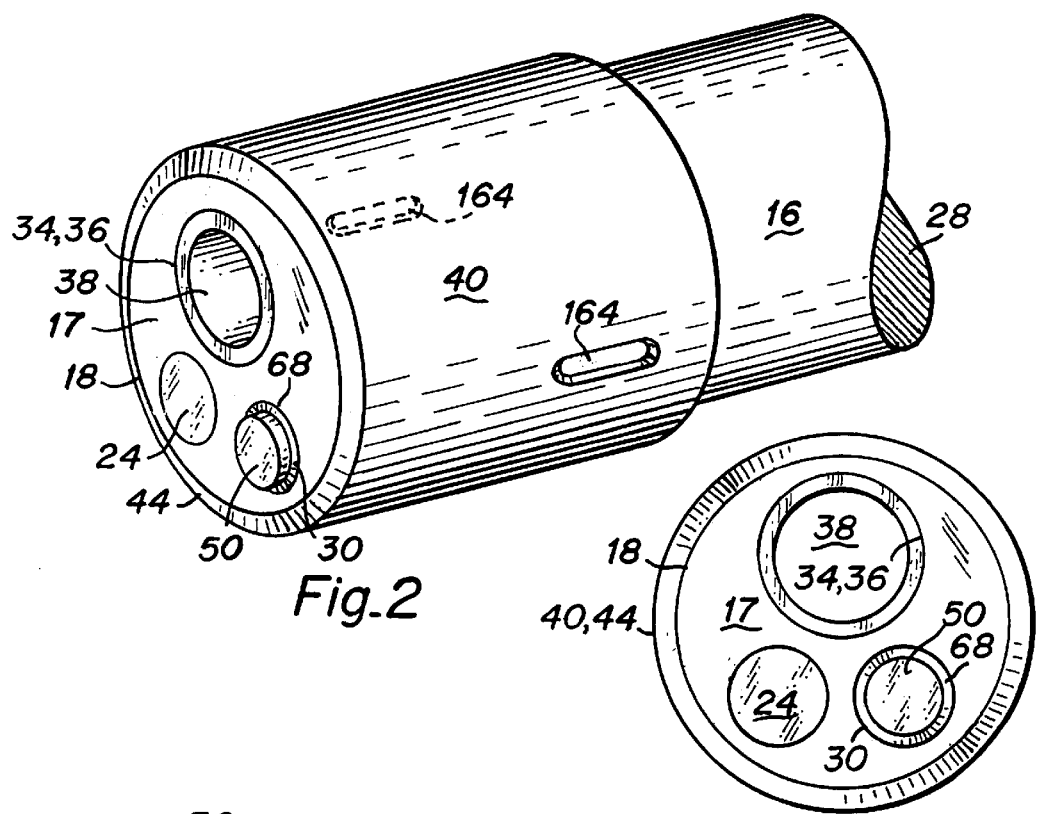
Fig. 2
Fig. 3
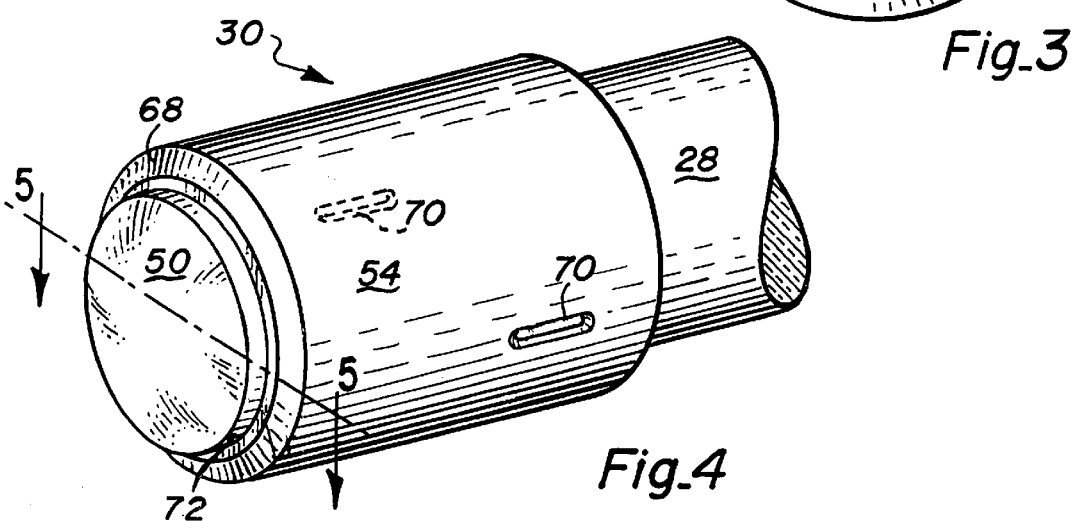
Fig. 4

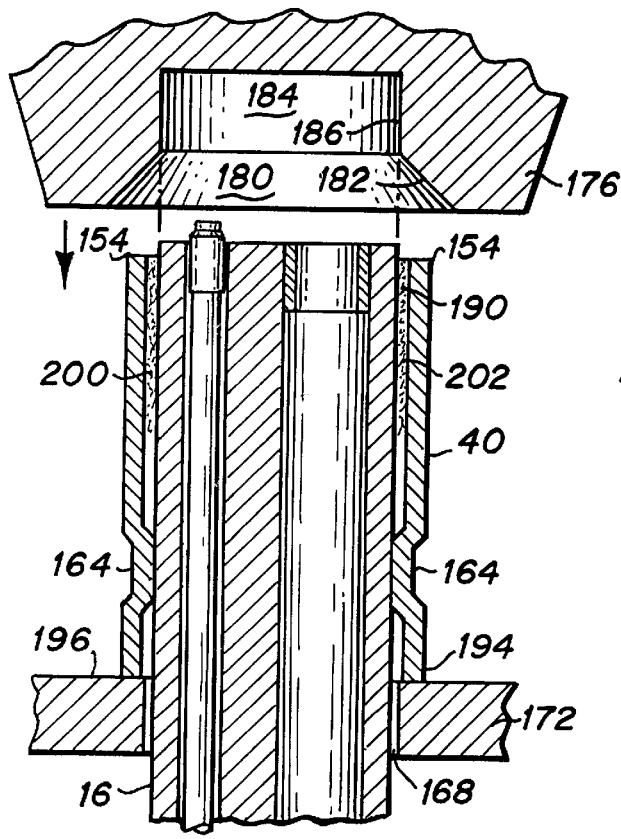
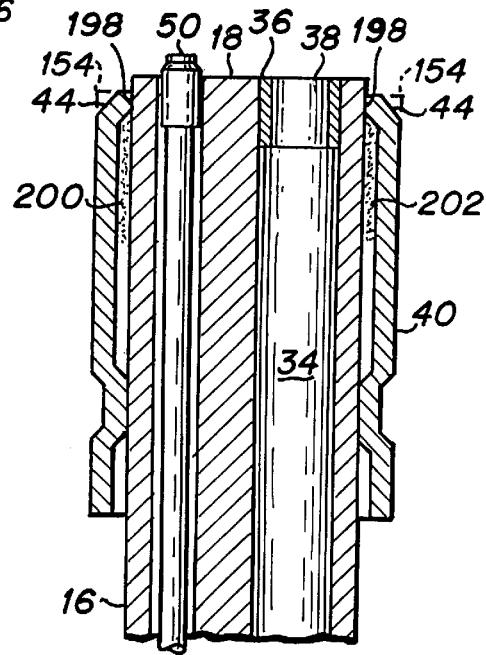
Fig.10  Fig.11
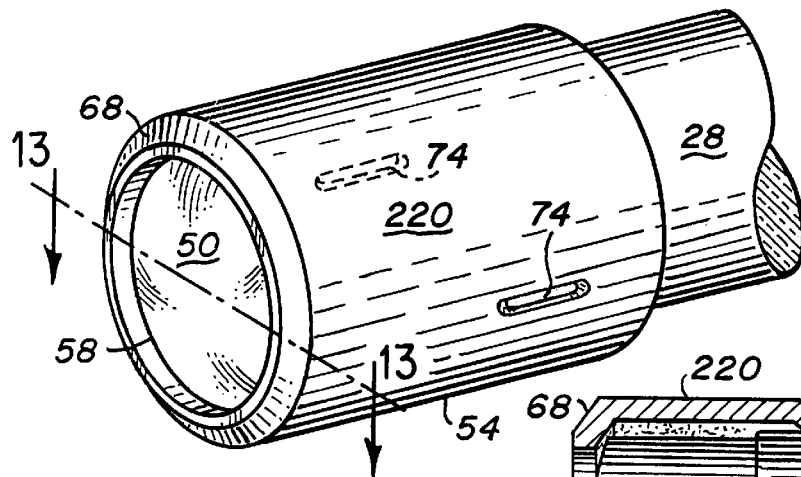
Fig.12
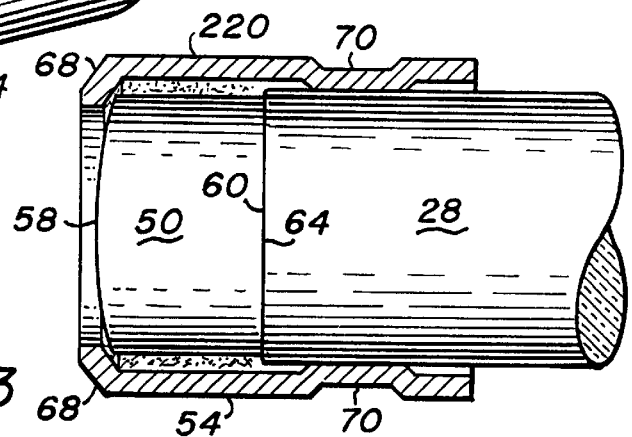
Fig.13

AUTOCLAVABLE ENDOSCOPE

BACKGROUND OF THE INVENTION

1. Field of the Invention

The present invention relates generally to flexible endoscopic probes, and more particularly to an endoscopic probe wherein an optical lens is mechanically engaged to the end of a coherent optical fiber at the tip of the probe, and wherein further component parts of the endoscope may also be engaged together at the tip of the probe utilizing a mechanical engagement means, such that the endoscope is structurally durable and can be repeatedly sterilized in an autoclave without damage to the endoscope and its components throughout its useful lifetime.

2. Description of the Prior Art

Prior art endoscopic probes contain a plurality of components disposed within a flexible tubular member. A typical prior art endoscopic probe is described in U.S. Pat. No. 5,456,245, issued Oct. 10, 1995 to Bornhop et al., entitled "Flexible Endoscope Probe and Method of Manufacture," in which potting materials and adhesives are used to engage various components at the tip of the probe and to seal the probe. A significant problem with such prior probes is infection control during usage of the probe, and the sterilization of such probes when they are used once. An article describing such infection control problem and the disinfecting or sterilizing of probes is printed in the American Journal of Infection Control, entitled "APIC Guidelines for Infection Prevention and Control in Flexible Endoscopy," Vol. 22, February, 1994, pages 19–38, written by M. A. Martin and M. Reichelderfer.

SUMMARY OF THE INVENTION

The flexible endoscopic probe of the present invention includes mechanically engaged components within the tip of the probe. That is, the probe includes a viewing system including a coherent optical fiber having a lens that is mechanically engaged to the tip thereof. Additionally, a metal sleeve may be utilized at the tip of the probe to mechanically bind all of the components within the probe at its tip. Potting materials or adhesives may also be utilized to seal the components within the probe tip. Owing to the usage of mechanical binding methods, the probe is more durable and may be heat sterilized in an autoclave, or the like, in order to permit repeated usage of the probe.

It is an advantage of the endoscopic probe of the present invention that it includes a lens component that is mechanically engaged to an optical fiber.

It is another advantage of the present invention that it includes a lens which is engaged to an optical fiber with a minimal use of sealants.

It is a further advantage of the present invention that all of the components of the endoscopic probe are engaged at the tip thereof utilizing a mechanical engagement means.

It is yet another advantage of the present invention that the components of the endoscopic probe are engaged at the tip thereof with a minimal use of sealants or potting materials.

It is yet a further advantage of the present invention that it may be repeatedly sterilized in an autoclave without significant degradation in its performance characteristics throughout the useful lifespan of the product.

These and other features and advantages of the present invention will become well understood upon reading the detailed description of the invention as set forth below.

IN THE DRAWINGS

FIG. 1 is a perspective view of the endoscopic probe system of the present invention;

FIG. 2 is an enlarged perspective view of the tip of the endoscopic probe of the present invention;

FIG. 3 is an end elevational view of the probe tip depicted in FIG. 2;

FIG. 4 is a perspective view of a first preferred embodiment of the tip of the optical fiber component of the endoscope of the present invention;

FIG. 10 is a side cross-sectional view of the endoscope tip of the present invention, depicting a further step in the manufacturing thereof;

FIG. 11 is a side cross-sectional of the tip of the endoscopic probe of the present invention upon completion of manufacturing;

FIG. 12 is a perspective view of an alternative embodiment of the tip of the optical fiber component of the endoscope of the present invention; and FIG. 13 is a side cross-sectional view of the tip depicted in FIG. 12, taken along lines 13—13 of FIG. 12.

DETAILED DESCRIPTION OF THE PREFERRED EMBODIMENTS

Figure 5:
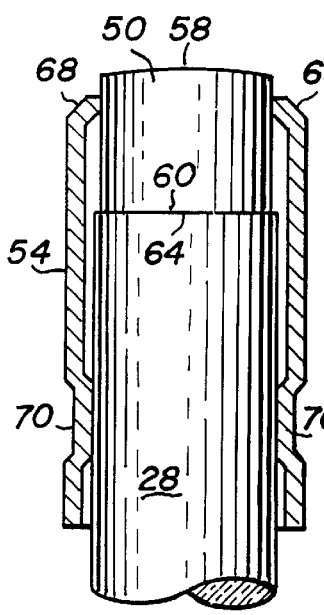
FIG. 5 is a side cross-sectional view of the tip of the optical fiber portion of the present invention, taken along lines 5—5 of FIG. 4.

FIG. 1 depicts the endoscopic probe system 10 of the present invention including a long, thin, flexible endoscopic probe 12 having a proximal end 14 and a distal end 16 which terminates in a probe tip 18. As is well known in the art the probe 12 is formed using a flexible extrusion tube 17, such as a PEBAX tube, having a plurality of tubular passages formed axially therewithin for the insertion of various components of the probe 12, from the proximal end 14 to the distal end 16; PEBAX is a trademark of Ato Shimie, Curbevole, France. The probe tip 18 comprises the end tip of the PEBAX tube 17 with various components as are herein described.

The probe system 10 includes an illumination system 19 including a light source 20 that projects viewing light through an optical fiber 22 to a light emitting tip 24 engaged in the tip 18 of the endoscopic probe 12. Such illumination systems 19 are well known in the prior art which also may include two or more light emitting optical fibers with individual tips. The probe system 10 also includes a viewing system 26 which receives imaging data through a coherent optical fiber 28 that passes through the probe 12 to a tip 30 disposed in the probe tip 18. The tip 30 includes an optical lens 50 as is known in the art. The system 10 may also include further components as are known in the art, such as an irrigation system 31 or a tissue sampling system 32 which operates through a hollow tubular passage 34 of the extrusion tube 17 and terminates at a passage tip 36. Such irrigation systems 31 and tissue sampling systems 32 are well known in the prior art. Also known in the prior art, and not depicted herein for clarity sake, are probe movement systems, such as wires that pass through the probe 12 to control the movement of the distal end 16 of the probe 12.

FIGS. 2 and 3 depict the distal end 16 of the probe 12, wherein FIG. 2 is an enlarged perspective view thereof and FIG. 3 is an end elevational view thereof. As depicted in FIGS. 2 and 3, the distal end 16 includes a cylindrical outer sleeve member 40 that surrounds and mechanically compresses the tip end 18 to hold the light emitting probe tip 24, the video imaging tip 30 and the tissue probe passage tip 36 within the extrusion tube 17. As can be seen from FIGS. 2 and 3, the sleeve 40 is radially inwardly mechanically deformed at its leading edge 44 to accomplish the mechanical holding of the tips 24, 30 and 36 together within the tip 18. A cylindrical sleeve 38 is preferably inserted within the tip 36 of the passage 34 to avoid compression of the walls of the flexible tube into the passage tip 36. The manufacturing process for creating the deformation of the edge 44 of the sleeve 40 to accomplish the mechanical holding of the three tips 24, 30 and 36 is discussed hereinbelow with the aid of FIGS. 8, 9 and 10.

FIGS. 4 and 5 depict a first preferred engagement method of the optical lens 50 to the coherent optical fiber 28, wherein FIG. 4 is a perspective view of the video imaging tip 30, and FIG. 5 is a side cross-sectional view taken along lines 5—5 of FIG. 4. The video imaging tip 30 includes the optical lens 50 that is fixedly engaged to the end of the coherent optical fiber 28 utilizing a mechanical engagement that is created by using a deformable sleeve 52 preferably composed of a metal such as a copper based alloy or gold or other suitable material as would be known to those skilled in the art. As depicted in FIGS. 4 and 5, optical lens 50 is preferably formed as a solid cylindrical lens body having a convex exterior surface 58 and a flat interior surface 60.

The interior face 60 of the lens 50 is butted against the end 64 of the coherent optical fiber 28. Such lenses 50 and coherent optical fibers 28 are well known in the endoscopic art, and are typically engaged together utilizing a transparent epoxy type adhesive. A significant feature of the present invention is that the lens 50 is mechanically engaged to the coherent optical fiber end 64 utilizing the cylindrical sleeve 54. To accomplish this mechanical engagement, the inner diameter of the cylindrical sleeve 54 closely matches the outer diameter of the optical fiber 28 and lens 50, such that a generally snug fit is obtained. The outer edge 68 of the sleeve 54 is mechanically deformed inwardly to frictionally engage the outer surface of the cylindrical lens 50, and the shaft of the sleeve 54 is crimped 70 to engage the coherent optical fiber 28. The preferred device to accomplish the mechanical deformation of the outer edge 68 of the sleeve 54 is disclosed in issued U.S. Pat. No. 5,305,406, the contents of which are incorporated herein as though set forth in full. The preferred method for the engagement of the lens 50 to the optical fiber end 64 utilizing the deformable cylindrical sleeve 54 is next discussed with the aid of FIGS. 6, 7 and 8.

Figure 6:
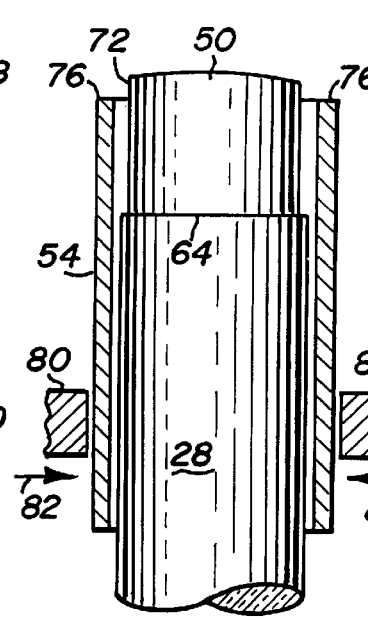
FIG. 6 is a side cross-sectional view depicting a step in the manufacturing of the optical fiber tip of the present invention.
Figure 8:
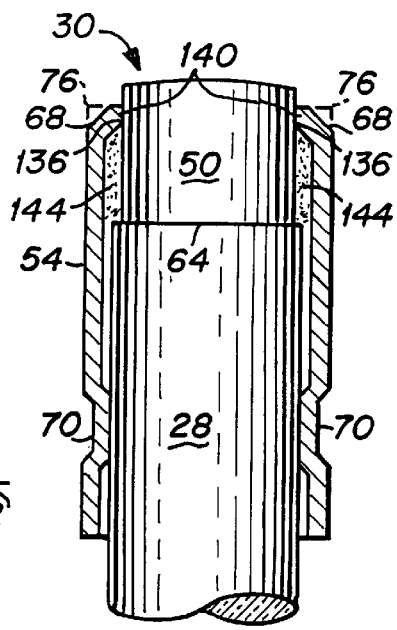
FIG. 8 is a side cross-sectional view of the optical fiber tip of the present invention at the completion of manufacturing.
Figure 7:
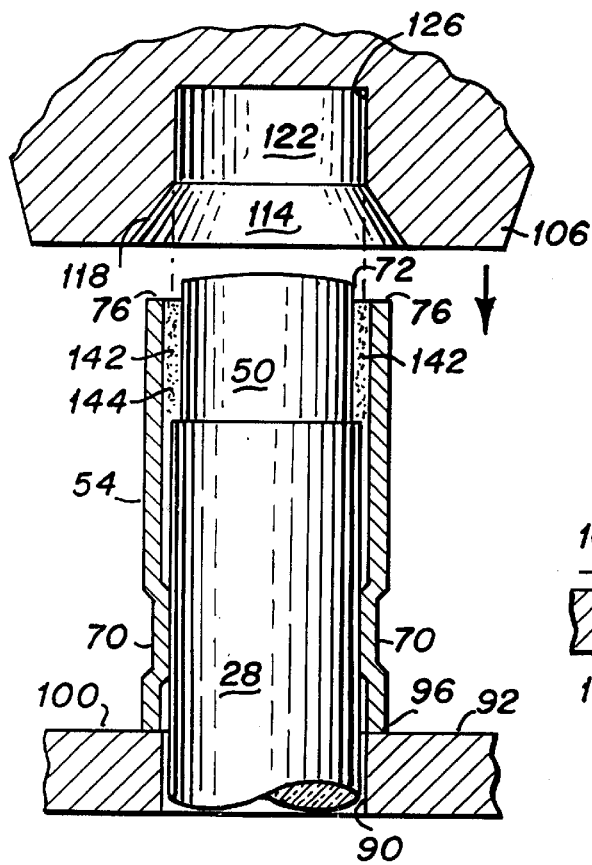
FIG. 7 is a side cross-sectional view depicting another step in the manufacturing of the optical fiber tip of the present invention.

FIGS. 6, 7 and 8 depict the manufacturing steps that are utilized in the preferred manufacturing method for the engagement of the lens 50 to the optical fiber end 64. Each of FIGS. 6, 7 and 8 is a cross-sectional view that is similar to FIG. 5, however, the optical fiber 26 and sleeve 54 are preferably oriented vertically to utilize gravitational force to simplify the assembly method. As depicted in FIG. 6, the cylindrical sleeve 54 is inserted over the end 64 of the coherent optical fiber 28. The sleeve 54 projects upwardly from the end 64 a sufficient distance such that the lens 50 may be placed within the sleeve 54. The sleeve 54 is then adjusted vertically, such that a small tip portion 72 of the lens 50 projects outwardly from the upper end 76 of the sleeve 54. When the sleeve 54 is in the proper vertical orientation to create the small lens projection 72, a standard crimping device 80 is utilized to provide a lateral force 82 against the sides of the sleeve 54 to depress the sleeve sides inwardly to form the crimp 70 (see FIG. 7), whereby the optical fiber 28 and the sleeve 54 become mechanically engaged together.

The outer end 76 of the sleeve 54 is next deformed (as sleeve end 68 is depicted in FIG. 5) to engage the lens 50 to the end 64 of the optical fiber 28. As is depicted in FIG. 7 the sleeve 54 is engaged to the optical fiber 28 by the crimp 70 and the lens 50 is loosely engaged in the outer end of the sleeve 54, such that a portion 72 of the lens 50 projects beyond the upper end 76 of the sleeve 54. As indicated hereinabove, an impact mounting assembly device, such as is described in U.S. Pat. No. 5,305,406 is next utilized to mechanically engage the lens 50 within the sleeve 54. The lens mounting method involves the placement of the optical fiber 28 with its crimp-attached sleeve 54 within a holding notch 90 formed in a holding member 92 of an impact assembly device, such that the rearward end 96 of the sleeve 54 rests against an inner surface 100 of the holding member 92, while the optical fiber 28 passes through the slot 90. Thereafter, an impact punch head 106 of the impact mounting device is moved into position 110 against the projecting distal end 76 of the sleeve 54. The impact head 106 is formed with a conical recess 114 defined by inwardly converging sidewalls 118. The sidewalls 118 converge to a cylindrical cavity 122 defined by sidewalls 126, which are dimensioned such that the diameter of the cylindrical cavity 122 is larger than the diameter of the lens 50. It is therefore to be understood that when the impact punch head 106 is forcefully directed 110 against the sleeve 54, that the sidewalls 118 of the conical cavity 114 will make an impact contact with the end 76 of the sleeve 54, while the lens 50 will project untouched into the cylindrical cavity 122. The contact of the rearward end 96 of the sleeve 54 with the surface 100 of the holding member 92 acts to prevent the sleeve 54 from moving rearwardly when it is impacted at the outer end 76 by the impact head 106.

FIG. 8 depicts the finished mechanical engagement of the lens 50 to the optical fiber 26. As shown in FIG. 8, the outer end 76 (now shown in phantom) of the sleeve 54 has been deformed to create the inwardly projecting end 68, wherein a deformed portion 136 of the tip of the sleeve 54 has been mechanically depressed inwardly into frictional engagement with the cylindrical side surface 140 of the lens 50. In this manner, the lens 50 is mechanically, frictionally engaged in a butted relationship with the end 64 of the optical fiber 28.

Various sealants and potting compounds that are well known to those skilled in the art can be advantageously utilized along with the mechanical engagement methods described hereabove. Specifically, a liquid sealant formulation 142 can be inserted into the circumferential gap 144 between the lens 50 and the sleeve 54, as depicted in FIG. 7. Thereafter, the outer end 76 of the sleeve 54 is deformed, as discussed above with regard to FIG. 8, and the sealant 142 thus remains within the gap 144 to provide a sealed mechanical engagement of the lens 50 within the sleeve 54.

Figure 9:
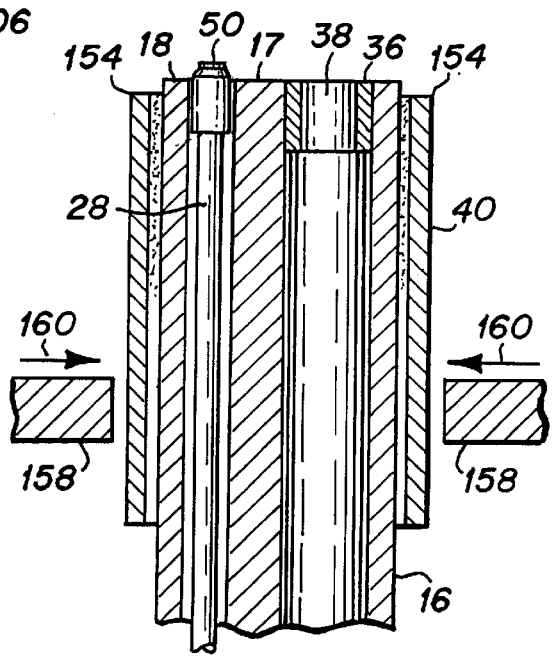
FIG. 9 is a side cross-sectional view of the endoscope tip of the present invention, depicting a step in the manufacturing thereof.

The manufacturing method for the endoscope of the present invention is depicted in FIGS. 9, 10 and 11, which manufacturing steps are similar to the manufacturing steps for the viewing system optical fiber probe tip 30. As depicted in FIG. 9, a sleeve 40 surrounds the distal end 16 of the endoscopic probe 12. The cylindrical sleeve 38 is disposed in the end 36 of the tubular passage 34, as discussed above, and the coherent optical fiber 28 with its mechanically engaged lens 50 projects through a tubular passage 150 axially formed through the PEBAX tube 17. The illumination optical fiber disposed within its tubular passageway is not depicted in the cross sectional view of FIG. 9. In the preferred endoscopic probe manufacturing method of the present invention, the cylindrical sleeve 40 is placed around the tip 16 of the probe 12 such that end 17 of the PEBAX tube projects slightly outwardly from the outer end 154 of the sleeve 40. A standard crimping means 158 is then utilized to apply a radially inward force 160 against the sides of the sleeve 40 to crimp 164 the sleeve 40 into a mechanical engagement with the tip 16 of the probe 12.

As depicted in FIG. 10, an impact mounting device is next utilized to further mechanically engage the sleeve 40 to the probe tip 16. As depicted in FIG. 10, the probe 12 with the sleeve 40 engaged by the crimp 164 is placed within a slot 168 formed in a holding member 172 of an impact mount device. A suitable impact mount device is described in U.S. Pat. No. 5,305,406, as has been mentioned and incorporated hereabove. An impact head 176 of the impact mounting device is next brought into contact with the upper end 154 of the sleeve 40. The impact head is formed with a conical cavity 180 defined by inwardly depending sidewalls 182 which terminate in a cylindrical cavity 184 defined by cylindrical sidewalls 186. It is to be understood that the diameter of the cylindrical cavity 184 is greater than the diameter of the tip 17 of the probe 12, whereas the conical sidewalls 182 will make impact contact with the upper end 154 of the sleeve 40. It is to be further understood that when the impact head 176 makes impact contact with the outer end 154 of the sleeve 40 that the outer end 154 will be deformed inwardly to make frictional contact with the outer surface 190 of the probe tip 16. The rearward end 194 of the sleeve 40 rests upon the surface 196 of the holding member 172, such that the sleeve is immovable during the impact head contact.

FIG. 11 depicts the probe tip 16 following the impact mounting of the sleeve 40. As depicted in FIG. 11, the sleeve end 154 (now shown in phantom) has been inwardly deformed, such that an inner portion 198 of the sleeve 40 makes frictional contact with the outer surface 190 of the probe tip 16, and the outer end 44 of the sleeve 40 is deformed, as previously described. In order to achieve a superior engagement of the impacted sleeve end 44 with the probe tip 16, the small cylindrical sleeve 38 is placed within the end 36 of the tube passage 34 prior to impact mounting. The sleeve 38 serves to provide mechanical rigidity to the outer end 36 of the tubular passage 34, which functions to prevent the collapse of the outer end 36 of the tubular passage 34 during impact mounting.

Various sealants and potting compounds that are well known to those skilled in the art can also be advantageously utilized along with the mechanical engagement methods described hereabove. Specifically, a liquid sealant formulation 200 can be inserted into the circumferential gap 202 between the surface 190 and the sleeve 40, as depicted in FIG. 10. Thereafter, the outer end 154 of the sleeve 40 is deformed, as discussed above with regard to FIG. 11, and the sealant 200 thus remains within the gap 202 to provide a sealed mechanical engagement of the probe tip 16 within the sleeve 40.

An alternative viewing lens tip 220 of the present invention is depicted in FIGS. 12 and 13, wherein FIG. 12 is a perspective view and FIG. 13 is a side cross-sectional view taken along lines 13—13 of FIG. 12. As depicted in FIGS. 12 and 13, a lens 50, being generally identical to lens 50 depicted FIGS. 4 and 5, and having a convex outer surface 58 and a plane inner surface 60 is butted against the end 64 of a coherent optical fiber 28. The lens 50 is held in position against the end 64 utilizing a deformable sleeve 54, as has been described hereabove with reference to FIGS. 4 and 5. The significant difference between this tip embodiment 220 and the tip embodiment 30 depicted in FIGS. 4 and 5 is that the lens 50 is contained within the deformed forward end 68 of the sleeve 54. That is, the lens 50 does not have an outwardly projecting portion 72 as depicted in FIGS. 4 and 5. Rather, the lens 50 is recessed within the crimped forward end 68 of the sleeve 54, as depicted in FIGS. 12 and 13. A method for manufacturing the tip 220 commences by deforming the forward edge 68 of the sleeve 54, preferably utilizing an impact mounting assembly device such as is described in U.S. Pat. No. 5,305,406. After the front end 68 of the sleeve 54 has been deformed, the lens 50 is placed within the sleeve 54, followed by the optical fiber 28. Thereafter, the sleeve 54 is crimped 70 to hold the sleeve and the optical fiber 28 together. In this manner, the lens 50 is mechanically held within the sleeve 54 in a butted relationship with the end 64 of the optical fiber 28.

It is therefore to be understood that the endoscopic probe 12 of the present invention includes the mechanical engagement of various components at the tip of the probe. The present invention is therefore repeatedly heat sterilizable utilizing an autoclave or similar apparatus, whereas prior art devices that use adhesives for primary engagement purposes cannot be repeatedly heat sterilized because of the adverse effect of heat upon the adhesives. It is to be further understood that the present invention includes both the impact mounting of the lens 50 to the optical fiber 28 in creating the imaging system, and the impact mounting of the outer sleeve 40 to the tip 18 of the probe 12 to securely engage the various components within the tip 18.

While the present invention has been shown and described with reference to certain preferred embodiments, it will be understood by those skilled in the art that certain alterations and modifications can be made herein without departing from the true spirit and scope of the invention. Therefore, the following claims are intended to be interpreted to cover all such altered and modified devices that nevertheless include the true spirit and scope of the invention.

What we claim is:

1. A fiberoptic viewing system probe comprising:
   a coherent optical fiber having a distal end;
   a lens member being engaged to said distal end of said optical fiber;
   a lens engagement means being mechanically engaged to said coherent optical fiber and mechanically engaged to said lens, and functioning to mechanically fixedly hold said lens to said distal end of said optical fiber.

2. A fiberoptic viewing system probe as described in claim 1 wherein said lens engagement means comprises the primary means for engagement of said lens to said distal end of said optical fiber.

3. A fiberoptic viewing system probe as described in claim 1 wherein said lens engagement means comprises a deformable cylindrical sleeve having a rearward end and a forward end having a forward edge thereof; said sleeve member being deformed proximate said rearward end to mechanically, frictionally engage said optical fiber, and said forward edge of said sleeve member being deformed to mechanically, frictionally engage said lens.

4. A fiberoptic viewing system probe as described in claim 3 wherein said forward edge is radially inwardly deformed.

5. A fiberoptic viewing system probe as described in claim 1 wherein said lens engagement means comprises a deformable cylindrical sleeve having a rearward end and a forward end having a forward edge thereof; said sleeve member being deformed proximate said rearward end to mechanically, frictionally engage said optical fiber, and said forward edge of said sleeve member being deformed to mechanically engage said lens.

6. An endoscopic probe comprising:

a flexible tubular member;

a fiberoptic viewing system probe being disposed within said flexible tubular member, said fiberoptic viewing system probe including a coherent optical fiber having a distal end;

a lens member being engaged to said distal end of said optical fiber;

a lens engagement means being mechanically engaged to said coherent optical fiber and mechanically engaged to said lens, and functioning to mechanically fixedly hold said lens to said distal end of said optical fiber.

7. An endoscopic probe as described in claim 6 wherein said lens engagement means comprises the primary means for engagement of said lens to said distal end of said optical fiber.

8. An endoscopic probe as described in claim 6 wherein said lens engagement means comprises a deformable cylindrical sleeve having a rearward end and a forward end having a forward edge thereof; said sleeve member being deformed proximate said rearward end to mechanically, frictionally engage said optical fiber, and said forward edge of said sleeve member being deformed to mechanically, frictionally engage said lens.

9. An endoscopic probe as described in claim 8 wherein said forward edge is radially inwardly deformed.

10. A fiberoptic viewing system probe as described in claim 6 wherein said lens engagement means comprises a deformable cylindrical sleeve having a rearward end and a forward end having a forward edge thereof; said sleeve member being deformed proximate said rearward end to mechanically, frictionally engage said optical fiber, and said forward edge of said sleeve member being deformed to mechanically engage said lens.

* * * * *